United States Patent
Garcia Ruiz et al.

(10) Patent No.: US 11,666,699 B1
(45) Date of Patent: Jun. 6, 2023

(54) PIERCING CONDUIT TO DELIVER MEDICATIONS TO A USER IN A PAINLESS METHOD

(71) Applicants: Julio Martin Garcia Ruiz, Miami, FL (US); Angie Rose Garcia Ruiz, Miami, FL (US)

(72) Inventors: Julio Martin Garcia Ruiz, Miami, FL (US); Angie Rose Garcia Ruiz, Miami, FL (US)

( * ) Notice: Subject to any disclaimer, the term of this patent is extended or adjusted under 35 U.S.C. 154(b) by 0 days.

(21) Appl. No.: 17/896,326

(22) Filed: Aug. 26, 2022

(51) Int. Cl.
*A61M 5/158* (2006.01)

(52) U.S. Cl.
CPC ..... *A61M 5/158* (2013.01); *A61M 2005/1586* (2013.01)

(58) Field of Classification Search
CPC ........ A61M 5/3287; A61M 2005/3289; A61M 5/42; A61M 5/422; A61M 5/425; A61M 5/427; A61M 5/158; A61M 2005/1586; A61M 2005/1585; A61M 5/32; A61M 5/3286; A61M 5/329; A61M 5/3291; A61M 5/3293; A61M 5/3295; A61M 5/46; A61M 5/3297; A61M 2005/3201; A61M 2025/0004; A61M 25/0067; A61M 25/0068; A61M 25/007; A61M 25/0097; A61M 25/01; A61M 2025/0175; A61M 25/06; A61M 25/065; A61B 17/0469; A61B 17/06
See application file for complete search history.

(56) References Cited

U.S. PATENT DOCUMENTS

| 4,527,564 A | 7/1985 | Eguchi et al. |
| 8,257,393 B2 | 9/2012 | Cichocki, Jr. |
| 2015/0217089 A1* | 8/2015 | Chuang ............... A61M 5/3287 604/506 |
| 2019/0046233 A1* | 2/2019 | Feng ................. A61M 39/0247 |

* cited by examiner

*Primary Examiner* — Kevin C Sirmons
*Assistant Examiner* — Avery Smale
(74) *Attorney, Agent, or Firm* — Sanchelima & Associates, P.A.; Christian Sanchelima; Jesus Sanchelima

(57) ABSTRACT

A piercing conduit to deliver medications to a user in a painless method including a placement phase, an inserting phase and an injection phase which are performed by the piercing conduit. The placement phase includes a penetrating bottom distal end of the piercing conduit which is inserted through a user's skin of the abdomen portion to place a middle aperture in the inside of the user's skin and then leave exposed the penetrating bottom distal end and a top distal end. The inserting phase passes through a sealing cap from the top distal end which has an aperture in which a needle is inserted along a conduit portion and then reaches the middle aperture that is placed inside of the user's skin. The injection phase delivers the medication with the syringe by the needle allowing to apply medication in a painless method. The piercing conduit is configured to be applied to users with constant medication such as diabetes or dialysis.

7 Claims, 6 Drawing Sheets

US 11,666,699 B1

PIERCING CONDUIT TO DELIVER MEDICATIONS TO A USER IN A PAINLESS METHOD

BACKGROUND OF THE INVENTION

1. Field of the Invention

The present invention relates to a piercing conduit to deliver medications to a user in a painless method and, more particularly, to a piercing conduit to deliver medications to a user in a painless method that is pierced through the skin of a user to then deliver medication with a syringe into a delivery opening along its periphery.

2. Description of the Related Art

Several designs for a piercing conduit to deliver medications to a user in a painless method have been designed in the past. None of them, however, include a piercing conduit to deliver medication therethrough in a painless method.

Applicant believes that a related reference corresponds to U.S. Pat. No. 8,257,393 issued for a piercing conduit member that passes through the skin to deliver medications disclosing pointed distal ends which are left outside the skin, and one or more openings along the length of the passageway of the device to deliver therapeutic fluids to the user. Applicant believes that another related reference corresponds to U.S. Pat. No. 4,527,564 issued for a curved needle for use in medical operations including a curved portion terminated with a needle. None of these references, however, teach of a piercing conduit member that passes through the skin to deliver medications comprising a top distal end that would be covered with a cap that can have one-way valve and a pointed bottom distal end, both are left exposed outside the skin, and an opening located towards the middle which remains on the side of the skin and the needle of the syringe exists through the opening to deliver the medication.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a piercing conduit to deliver medications with a painless method.

It is another of the objects of the present invention to provide an accessible method to deliver medication by oneself.

It is another object of this invention to provide a conduit member having a top distal end with a one-way valve and an impermeable seal.

It is still another object of the present invention to provide a middle aperture to allow the needle reach the skin of the user.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
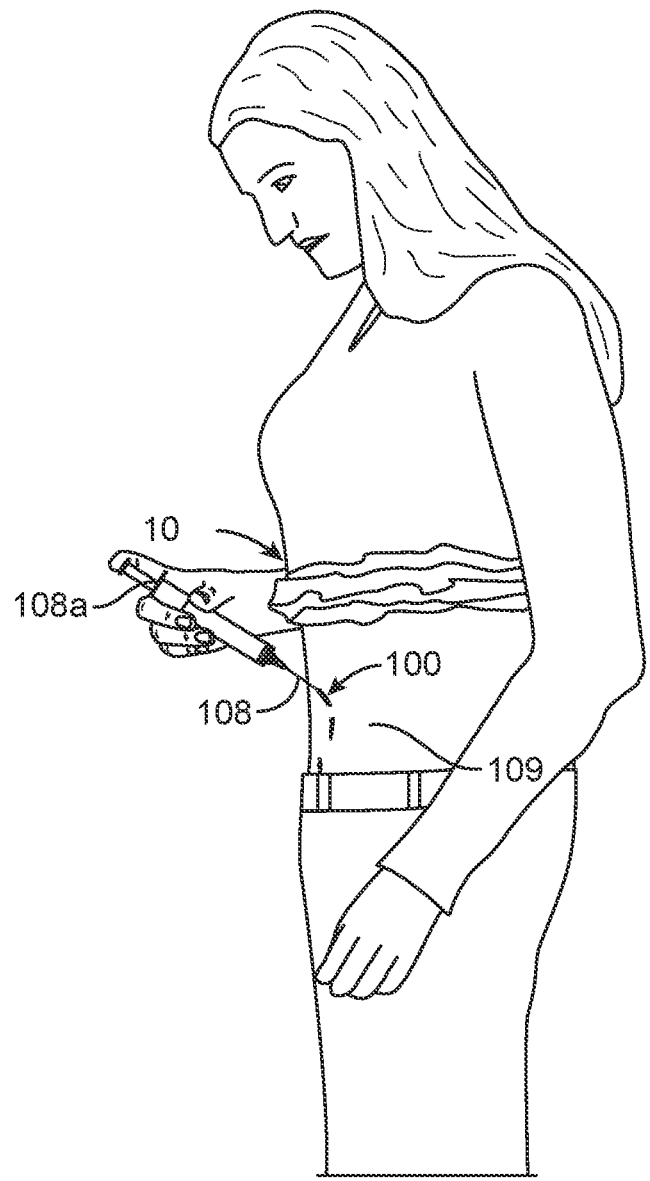
FIG. 1 represents an operational view of the present invention 10 showing a piercing conduit 100 embedded into the skin 109 wherein a user is applying medication therein with a syringe 108a and a needle 108a inserted to the piercing conduit 100.

Referring now to the drawings, where the present invention is generally referred to with numeral 10, it can be observed that it basically includes a placement phase 20, an inserting phase 40 and an injection phase 60, and a piercing conduit 100. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Figure 3:
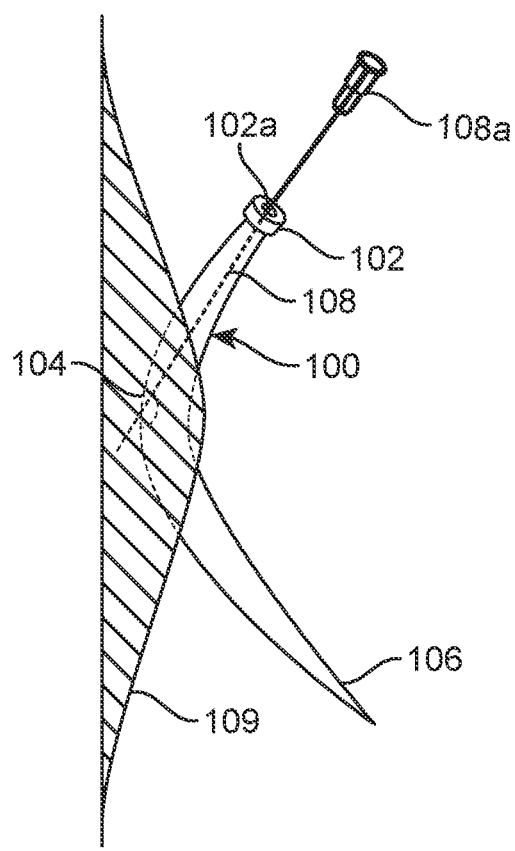
FIG. 3 is a representation of a rear view of the piercing conduit 100 wherein is shown a middle portion 104 in the inner of the user's skin 109 and a syringe 108a is inserted through the sealing cap 102 and the top distal end 102.
Figure 4:
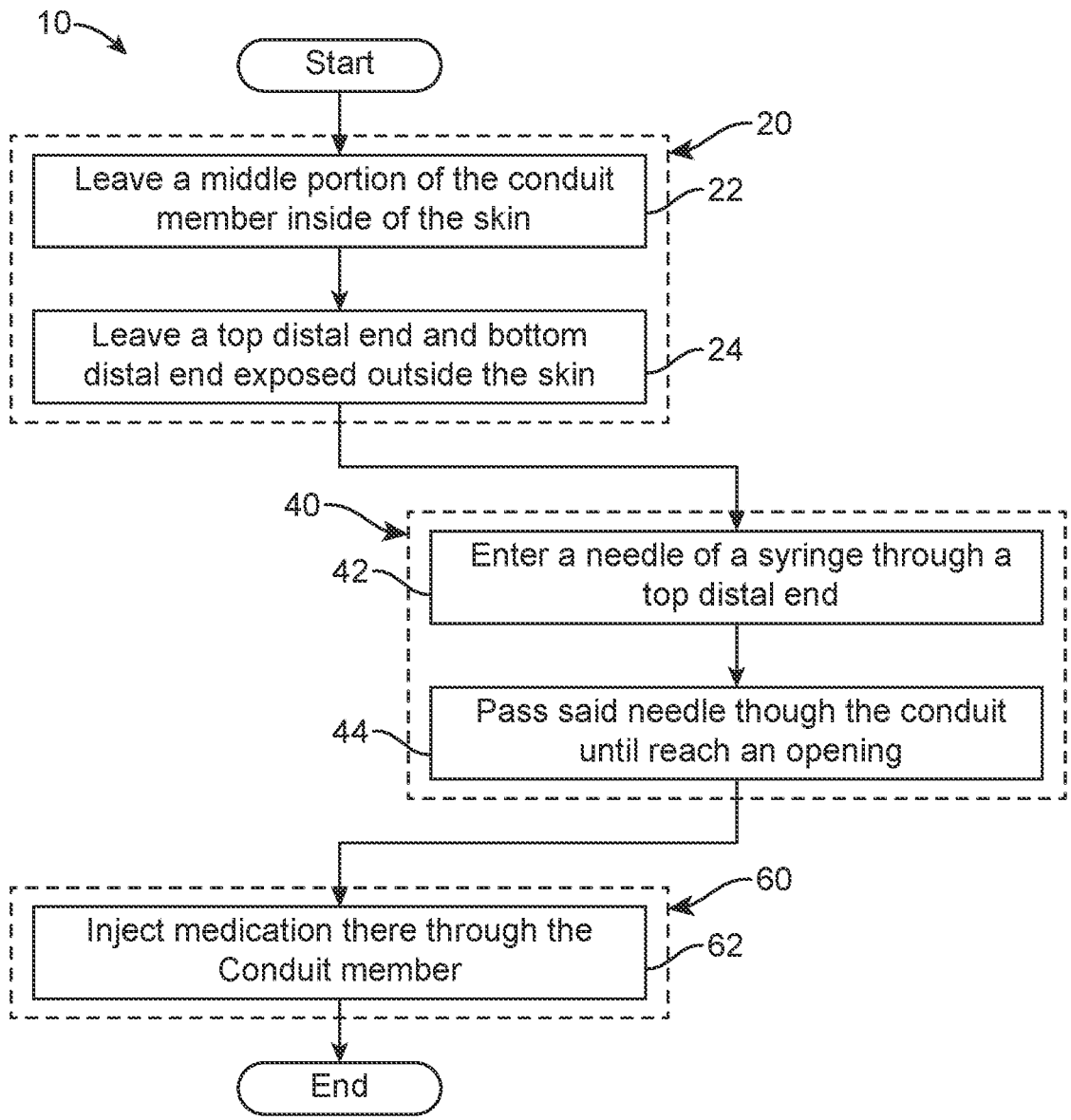
FIG. 4 illustrates a flow chart for a method and system 10 containing a first step 20 and a second step 40.

The placement phase 20 includes a first step 22 and a second step 24. The first step 20. It is to be considered that the piercing conduit 100 may use a method 10 which has the placement phase 20, the inserting phase 40 and the injection phase 60. In a suitable embodiment the disclosed system allows a user to insert medication through the piercing conduit 100 by said method 10. In a preferred embodiment, the first step 22 may be leaving a middle portion of the piercing conduit 100 inside of a user's skin 109. In one embodiment, the user's skin 109 may be an adipose tissue or a user's belly considering also an abdominal area of a user. The adipose tissue is a region of the skin that does not have a high degree of pain when injecting medication thereof. It is to be understood that the piercing conduit 100 may be suitable to be inserted through the user's skin 109 as illustrated in FIG. 3 wherein a middle aperture 104 is attached in the inside of the user's skin 109 and may be configured as an exit for medication. In a suitable embodiment a penetrating bottom distal end 106 may be inserted through the user's skin 109 when middle aperture 104 is attached to the user's skin 109 the bottom distal end 106 then passes through a bottom portion of the user's skin 109 wherein the bottom distal end 106 was first inserted to be set as shown in FIG. 3. The bottom distal end 106 may be made of a surgical steel as the top distal end 102 and the middle aperture 104.

Figure 2:
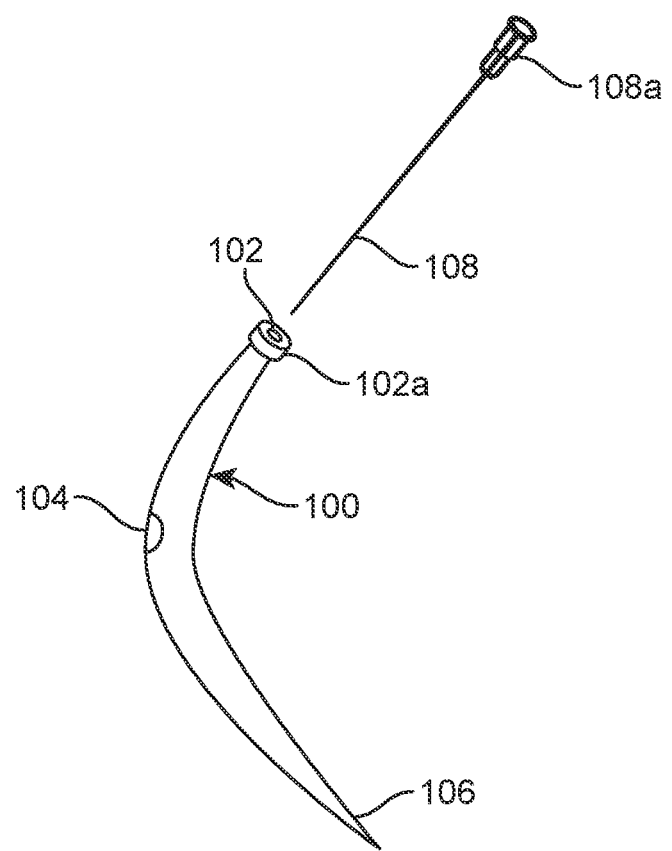
FIG. 2 shows an isometric view of the piercing conduit 100. A cap 102a is mounted on a top distal end 102.

The method further includes the second step 24 which may be leaving a top distal end 102 and the bottom distal end 106 exposed outside the user's skin 109 when leaving the middle aperture 104 inside the user's skin 109. Leaving the top distal end 102 and the bottom distal end 106 exposed outside the user's skin 109 may allow use the user to wear the piercing conduit 100. In a suitable embodiment, the bottom distal end 106 may have a pointed end allowing to insert the bottom distal end through the user's skin 109. In a preferred embodiment, the top distal end 102 may be internally connected with the middle aperture 104. The piercing conduit 100 may be suitable to be made of a titanium and surgical steel. In a preferred embodiment, the piercing conduit 100 may have a curved body as best shown in FIG. 2 and FIG. 3. It should be considered that top distal end 102 may be made of a titanium and surgical steel, or a similar material as the piercing conduit 100 may be made of. It also should be considered that middle aperture 104 may be made of a surgical steel.

Figure 5:
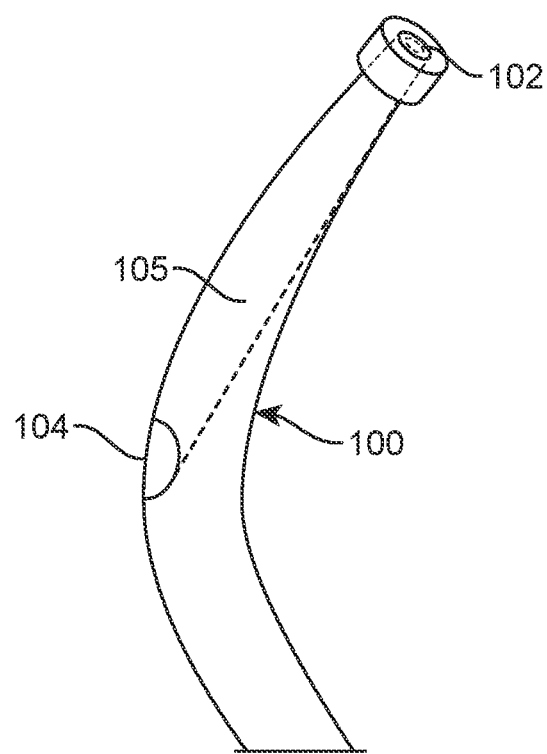
FIG. 5 shows an enlarged view of the top distal end 102 and the middle portion 104 which are related by a hollow portion 105.
Figure 6:
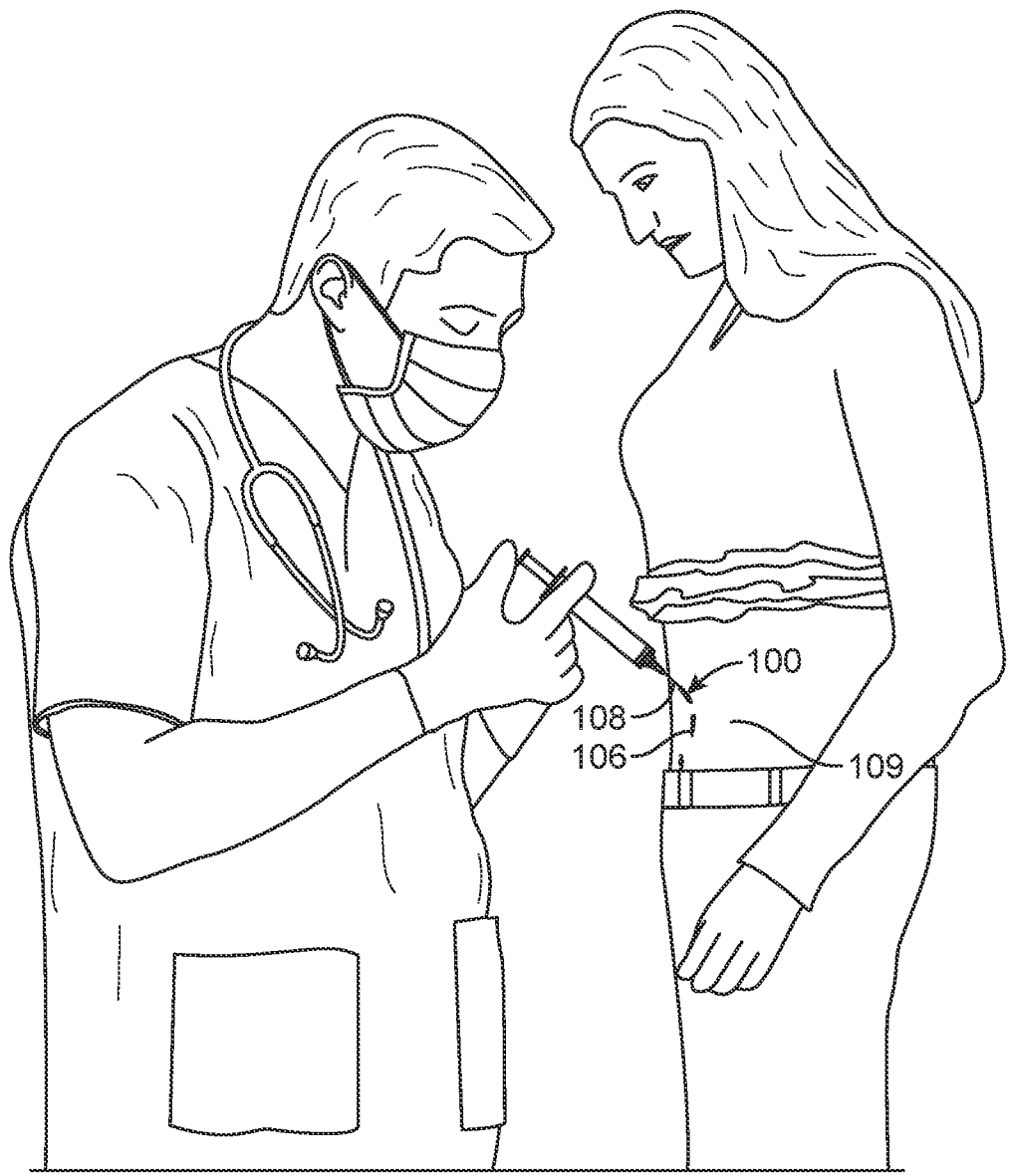
FIG. 6 depicts an exemplary operational view of the present invention where a user is being assisted by a doctor to apply medication through the piercing conduit 100.

The inserting phase 40 includes a third step 42 and a fourth step 44. The third step 42 may be entering a needle 108 of a syringe 108a when middle portion 104 remains on the inside of the user's skin 109. It is to be considered that third step 42 is implemented after passing through a sealing cap 102a which is placed in the top distal end 102 wherein the syringe 108a and the needle 108 passes through a hollow portion 105. The sealing cap 102 may be made of an impermeable seal and may be configured to seal and avoid collecting debris on the top distal end 102. The sealing cap 102a may be suitable to have a shape that conforms with the shape of the top distal end 102 and surround thereof. It may be understood that the sealing cap 102a is mounted from the top distal end 102 and the needle 108 which is configured to deliver medication may be inserted through the top distal end 102 and the sealing cap 102a along the hollow portion 105 which can be shown in FIG. 5. Another embodiment during the entering phase 40 is passing the needle 108 through the hollow portion 105 until reaching the middle aperture 104 passing through into the user's skin 109 as best illustrated in FIG. 2 which may be the fourth step 44. In a suitable embodiment fourth step 44 may allow the user to receive an injection in a painless way. In a suitable embodiment, top distal end 102 may have a shape that conforms with the needle 108. In another preferred embodiment, the piercing conduit 100 may have a hollow portion which is placed wherein the hollow portion 105 allowing inserting the needle 108.

The injection phase 60 includes a fifth step 62. The fifth step 62 may be injecting medication therethrough the hollow portion 105, when needle 108 reach the middle aperture 104. Injecting medication may be suitable when the needle 108 exits through the middle aperture 104. It may be suitable to inject any suitable solution for the embodiment when the piercing conduit may be placed through the user's skin 109 in an abdominal portion thereof. The fifth step 62 may allow the user to receive medication in a painless way by method 10. It may be understood that the piercing conduit 100 may be configured to be attached to the adipose tissue or a user's belly considering also the abdominal area of a user wherein a user may be able to apply the medication by her/his own as best observed in FIG. 1. The piercing conduit 100 may be focused on users with constant medication such diabetes or dialysis.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A piercing conduit to deliver a medication to a user, comprising:
a curved piercing conduit having a top end with an opening configured to receive a syringe, a bottom end, and a central portion located on a midpoint between the top end and the bottom end, wherein said central portion has a bigger diameter than a diameter of said bottom end and said top end, wherein said piercing conduit includes a delivery opening, said delivery opening is located on said central portion, wherein said bottom end is sharp, wherein said bottom end is configured to penetrate skin of said user, wherein said piercing conduit is configured to be inserted in said skin of said user having said bottom end and said top end exposed and said delivery opening within said user, wherein said opening is fluidically connected with said delivery opening by means of a hollow portion, wherein said hollow portion is within said piercing conduit, said hollow portion extends from said opening to said delivery opening, said delivery opening located along a periphery of said piercing conduit in a relationship that cooperates with said top end so that said syringe is passed through said delivery opening after being inserted through said top end, said delivery opening is configured to permit said syringe to penetrate inside said skin of said user therefrom, wherein said top end includes a sealing cap adapted to be passed through and to be concentrically placed around said top end, wherein said sealing cap is made of an impermeable seal, said sealing cap is configured to seal and avoid collecting debris on said top end-.

2. The piercing conduit of claim 1 wherein said delivery opening is configured to point toward an interior of the user while said top end and said bottom end configured to point toward an exterior of the user.

3. The piercing conduit of claim 1, wherein said top end has a circular shape that conforms with a body of a needle when inserting the needle through the top end.

4. The piercing conduit of claim 1, wherein a needle is configured to be inserted by the syringe through the piercing conduit.

5. The piercing conduit of claim 1, wherein a needle of the syringe is configured to be inserted through the delivery opening before delivering the medication.

6. A piercing conduit to deliver a medication to a user, comprising:
a curved piercing conduit having a top end with an opening configured to receive a syringe, a bottom end, and a central portion located on a midpoint between the top end and the bottom end, wherein said central portion has a bigger diameter than a diameter of said bottom end and said top end, wherein said piercing conduit includes a delivery opening, said delivery opening is located on said central portion, wherein said bottom end is sharp, wherein said bottom end is configured to penetrate skin of a said user, wherein said piercing conduit is configured to be inserted in said skin of said user having said bottom end and said top end exposed and said delivery opening within said user, wherein said opening is fluidically connected with said delivery opening by means of a hollow portion, wherein said hollow portion is within said piercing conduit, said hollow portion extends from said opening to said delivery opening, said delivery opening located along a periphery of said piercing conduit in a relationship that cooperates with said top end so that said syringe is passed through said delivery opening after being inserted through said top end, said delivery opening is configured to permit said syringe to penetrate inside said skin of said user therefrom, wherein said top end includes a sealing cap adapted to be passed through and to be concentrically placed around said top end, wherein said sealing cap is made of an impermeable seal, said sealing cap is configured to seal and avoid collecting debris on said top end, said piercing conduit configured as a medical applicator device for frequent users of the medication;

wherein, in a placement phase, the piercing conduit is configured to be pierced through the skin of the user, and wherein the top end and the bottom end are exposed outside of the skin of the user while the central portion of the piercing conduit is configured to remain beneath the skin of the user;

wherein, in an inserting phase, a needle of the syringe is configured to be passed through the opening of the top end, through said hollow portion of the piercing conduit, and through the delivery opening in the central portion of the piercing conduit; and wherein, in an injection phase, the medication is injected by the syringe through the needle to deliver the medication through said delivery opening.

7. A piercing conduit to deliver a medication to a user, consisting of: a curved piercing conduit having a top end with an opening configured to receive a syringe, a bottom end, and a central portion located on a midpoint between the top end and the bottom end, wherein said piercing conduit is made of titanium and surgical steel, wherein said central portion has a bigger diameter than a diameter of said bottom end and said top end, wherein said piercing conduit includes a delivery opening, said delivery opening is located on said central portion, wherein said bottom end is sharp, wherein said bottom end is configured to penetrate skin of said user, wherein said piercing conduit is configured to be inserted in said skin of said user having said bottom end and said top end exposed and said delivery opening within said user, wherein said opening is fluidically connected with said delivery opening by means of a hollow portion, wherein said hollow portion is within said piercing conduit, said hollow portion extends from said opening to said delivery opening, said delivery opening located along a periphery of said piercing conduit in a relationship that cooperates with said top end so that said syringe is passed through said delivery opening after being inserted through said top end, said delivery opening is configured to permit said syringe to penetrate inside a body of the user, said piercing conduit configured as a medical applicator device for frequent users of the medication, wherein said top end includes a sealing cap adapted to be passed through and to be concentrically placed around said top end, wherein said sealing cap is made of an impermeable seal, said sealing cap is configured to seal and avoid collecting debris on said top end;

wherein, in a placement phase, the piercing conduit is configured to be pierced through said skin of said user, and wherein the top end and the bottom end are exposed outside of the skin of the user while the central portion of the piercing conduit is configured to remain beneath the skin of the user, wherein, in an inserting phase, a needle of the syringe is configured to be passed through said sealing cap, said sealing cap is a one-way valve, through said hollow portion of the piercing conduit, and through the delivery opening in the central portion of the piercing conduit, the one-way valve causing the piercing conduit to be hygienic; and wherein, in an injection phase, the medication is injected by the syringe through the needle to deliver the medication through said delivery opening.

* * * * *